(12) United States Patent
Li et al.

(10) Patent No.: US 10,945,685 B2
(45) Date of Patent: Mar. 16, 2021

(54) SYSTEM AND METHOD FOR NORMALIZING STANDARDIZED UPTAKE VALUES IN BRAIN POSITRON EMISSION TOMOGRAPHY (PET) IMAGES

(71) Applicant: New York University, New York, NY (US)

(72) Inventors: Yi Li, Harrison, NJ (US); Jingyun Chen, East Rutherford, NJ (US); Mony De Leon, New York, NY (US)

(73) Assignee: New York University, New York, NY (US)

( * ) Notice: Subject to any disclaimer, the term of this patent is extended or adjusted under 35 U.S.C. 154(b) by 15 days.

(21) Appl. No.: 16/521,261

(22) Filed: Jul. 24, 2019

(65) Prior Publication Data

US 2020/0029918 A1 Jan. 30, 2020

Related U.S. Application Data

(60) Provisional application No. 62/702,972, filed on Jul. 25, 2018.

(51) Int. Cl.
*A61B 6/03* (2006.01)
*G06T 5/40* (2006.01)
(Continued)

(52) U.S. Cl.
CPC .......... *A61B 6/037* (2013.01); *G01T 1/2985* (2013.01); *G06T 5/40* (2013.01); *G06T 5/50* (2013.01);
(Continued)

(58) Field of Classification Search
CPC ....... A61B 6/037; A61B 6/501; G01T 1/2985; G06T 2207/10081; G06T 2207/10104;
(Continued)

(56) References Cited

U.S. PATENT DOCUMENTS

2014/0307936 A1* 10/2014 Dore ..................... G06T 7/0016
382/131
2016/0166229 A1* 6/2016 Matthews .............. A61B 6/037
600/431

(Continued)

OTHER PUBLICATIONS

Chen et al., "Comparing quantitative measures of global and regional tau binding for 18F-AV-1451 PET scans", J Nucl. Med, May 1, 2019, vol. 60, No. supplement 1,1628.
(Continued)

*Primary Examiner* — Mark R Gaworecki
(74) *Attorney, Agent, or Firm* — Fay Kaplun & Marcin, LLP

(57) ABSTRACT

Systems and methods are for analyzing Positron Emission Tomography (PET) image data. The methods may include generating a set of standardized uptake values (SUVs) of global or localized PET data for voxels within a selected region of interest (ROI), normalizing the set of SUVs by generating a set of SUVPs where each corresponding SUVP for each SUV is obtained using the formula: SUVP=(SUV−M)/S, wherein M corresponds to a peak value for the set of SUVs, and S corresponds to a spread for the set of SUVs, and generating a normalized image based on the set of SUVPs for the ROI. The systems may include any suitable device for PET image analysis performing the methods.

10 Claims, 8 Drawing Sheets

(51) Int. Cl.
  *G06T 5/50* (2006.01)
  *G01T 1/29* (2006.01)
  *G06T 7/00* (2017.01)
  *A61B 6/00* (2006.01)

(52) U.S. Cl.
  CPC ............ *G06T 7/0012* (2013.01); *A61B 6/501* (2013.01); *G06T 2207/10104* (2013.01); *G06T 2207/30016* (2013.01)

(58) Field of Classification Search
  CPC . G06T 2207/30016; G06T 5/007; G06T 5/40; G06T 5/50; G06T 7/0012
  See application file for complete search history.

(56) References Cited

U.S. PATENT DOCUMENTS

| | | | |
|---|---|---|---|
| 2016/0239966 A1* | 8/2016 | Parsey | A61B 5/16 |
| 2017/0371046 A1* | 12/2017 | Laurence | G01T 1/249 |
| 2018/0204327 A1* | 7/2018 | Matthews | G06K 9/00147 |
| 2019/0259159 A1* | 8/2019 | Udupa | A61B 6/5217 |

OTHER PUBLICATIONS

Chen et al., "Quantitative evaluation of tau PET tracers 18F-THK5351 and 18F-AV-1451 in Alzheimer's disease with standardized uptake value peak-alignment (SUVP) normalization," European Journal of Nuclear Medicine and Molecular Imaging, (2018), 45:1596-1604 (Published online Apr. 27, 2018).

* cited by examiner

SYSTEM AND METHOD FOR NORMALIZING STANDARDIZED UPTAKE VALUES IN BRAIN POSITRON EMISSION TOMOGRAPHY (PET) IMAGES

PRIORITY CLAIM

The present application claims priority to U.S. Provisional Application Ser. No. 62/702,972 entitled "System and Method for Normalizing Standardized Uptake Values in Brain Positron Emission Tomography (PET) Images" filed on Jul. 25, 2018, the entire contents of which is hereby incorporated by reference herein.

GOVERNMENT FUNDING

This invention was made with government support under NIH/NIA grants AG035137, AG032554, AG022374, and AG13616, AG12101, AG08051, NIH-HLB HL111724. The U.S. Government has certain rights in the invention.

BACKGROUND

Off-target binding is a common issue in PET scan. Especially recent tau PET, such as $^{18}$F-THK5351 and $^{18}$F-AV-1451. Recent data showed widespread Monoamine oxidase B (MAO-B) binding of THK5351 that could impact interpretation, and some Monoamine oxidase A (MAO-A) binding of AV-1451, but details remained unclear. While off-target binding does not necessarily invalidate a tracer, there is a lack of a valid tool to fully characterize them. Further, the tracer's utilization would be limited by SUVR method if conventional reference region was affected by off-target binding.

PET tracers are useful in observing in vivo biological processes and have been developed to assist in diagnosis of specific pathology. Quantitative evaluation of PET images has always been a challenge. The Standardized Uptake Value (SUV) quantifies radiotracer uptake in clinical PET scans. This value is computed from the number of counts of emission events recorded per voxel in the image reconstructed from event data captured in the PET scan. Raw SUV scan data may be expressed in units of MBq/ml and calculated as:

$$SUV = \frac{\text{PET scan data (in } MBq/\text{ml)} \times \text{patient mass (in grams)}}{\text{total injected dose (in } MBq)}$$

The measurements in raw PET image is relative not absolute, and therefore can't be compared directly. Normalization method is necessary for investigating and comparing the standardized uptake values (SUV), or counts, of PET scans among different subjects. The conventional standard uptake value ratio (SUVR) normalization method divides raw SUV from PET scans by a reference value, which is typically the mean SUV within the cerebellum gray matter (CGM), to arrive at a normalized value. However, this SUVR normalization method is subject to bias because of variations in the reference values used. Specifically, SUVR normalizes the raw SUV from PET scans using the mean SUV from a reference region, typically from within the CGM, from the same patient. Variations in the reference region's signal can cause underestimation or overestimation of real group difference after normalization. In particular, variations of the signal observed in the reference region for SUVR, which is the cerebellum, is particularly different in tau PET studies, such as VA-1451, THK5351 and MK6240 PET images. Cerebellum showed off target binding in those PET images, causing underestimation or overestimation of real group difference after normalization. Previous amyloid PET failed to show longitudinal affect in disease progression and treatment, may be partially due to the signal variation of reference region.

Another disadvantage of the SUVR method is its range and cutoff values varies among different tracers and PET scanners, making it challenging to distinguish positive uptake (binding).

All those problems indicate the limitation of conventional standard uptake value ratio (SUVR) method.

SUMMARY OF THE INVENTION

One of embodiments of the present invention provides a method for analyzing Positron Emission Tomography (PET) image data. The method comprises localizing the PET data with at least one image mask to generate localized PET data. The PET data may be co-registered to correspond to anatomical structures represented by the image mask. The image mask may comprise anatomical image data of the corresponding anatomical structures (e.g., magnetic resonance image (MRI) and/or a computed tomography (CT) data). The method further comprises generating a set of image intensity values (Ps) based on localized PET data for voxels within a selected region of interest (ROI). The ROI may correspond to any predetermined portion of a patient's body. For example, ROI may correspond to a portion of a brain. As another example, the ROI may correspond to an entire brain, in which case global PET data (i.e., PET data for an entire brain may be analyzed according to the method described herein). Although the discussions below relate to analysis of PET image data for a portion or an entire brain, it is contemplated that the method described herein may be suitable for analyzing PET image data for any portion of a patient's body. Each of the image intensity values (Ps) corresponds to an intensity of the localized PET data for a corresponding one of the voxels. A histogram of a set of image intensity values (Ps) within the ROI is generated, and a Gaussian curve is fit to the histogram. The method also comprises normalizing the set of image intensity values (Ps) by generating a set of normalized values (Ns) where each corresponding N for each P is obtained using the formula: N=(P−M)/S, wherein M corresponds to a peak value for the set of image intensity values (Ps), and S corresponds to a spread for the set of image intensity values (Ps), and generating a normalized image based on the set of normalized values (Ns). Alternatively, M is defined as the mean while S is the standard deviation of the Gaussian distribution derived from the fit curve in the previous step. The image intensity values (Ps) may be standardized uptake values (SUVs) to generate SUVPs (as discussed further below) as its normalized values (Ns). To generate the regional SUVP value, a threshold value is necessary to exclude negative values. The general cut off value is 0. Normalized values (Ns)>0 will be used to calculate the regional SUVP value.

A system for implementing the method described above is also contemplated. The system may comprise any suitable device for PET image analysis performing the method described above. For example, a system for generating a normalized Positron Emission Tomography (PET) image may be provided. A Positron Emission Tomography (PET) image system may be provided. The system comprises an imaging device configured to detect radioactive emissions from a patient for a predetermined period of time, the device further configured to generate PET data based on the detected radioactive emissions. The system also comprises a memory storage device configured to store the PET data. The system further comprises a processing arrangement configured to localize the PET data with at least one image mask to generate localized PET data, the PET data be co-registered to correspond to anatomical structures represented by the image mask, the processing arrangement further configured to generate set of image intensity values (Ps) based on the localized PET data for voxels within a selected region of interest (ROI), each of the image intensity values corresponding to an intensity of the PET data for a corresponding one of the voxels, normalize the set of image intensity values (Ps) by generating a set of normalized values (Ns) where each corresponding N for each P is obtained using the formula: N=(P−M)/S, wherein M corresponds to a peak value for the set of image intensity values (Ps), and S corresponds to a spread for the set of image intensity values (Ps), and the processing arrangement further configured to generate a normalized PET image based on the set of normalized values (Ns).

These and other aspects of the invention will become apparent to those skilled in the art after a reading of the following detailed description of the invention, including the figures and appended claims.

DETAILED DESCRIPTION

The present invention provides a method for normalizing image intensity data corresponding voxels within a PET scan to improve quantitative PET data analysis. The description below are directed to analysis of a particular type of image intensity data, e.g., standardized uptake values (SUVs) to generate normalized values, e.g., standardized uptake value peak-alignment (SUVP). However, it is contemplated that the normalization methods described herein may be applied to any suitable image intensity data, e.g., raw PET intensity data. In particular, any suitable image intensity data may be analyzed using a peak-alignment method as described below to generate normalized data for quantitative PET data analysis.

The present invention provides a method for normalizing raw SUV from PET scans that reduces bias in quantitative PET data analysis, and enhance the disease related signal. In one example, the method is a standardized uptake value peak-alignment (SUVP) method that provides an unbiased estimation of the regional distribution patterns of Standardized Uptake Values (SUV) to more robustly analyze the regional distribution patterns. The SUVP method may provide a more robust analysis of the regional distribution patterns, including in areas that have conventionally been used as reference regions, e.g., the cerebellum.

Figure 1:
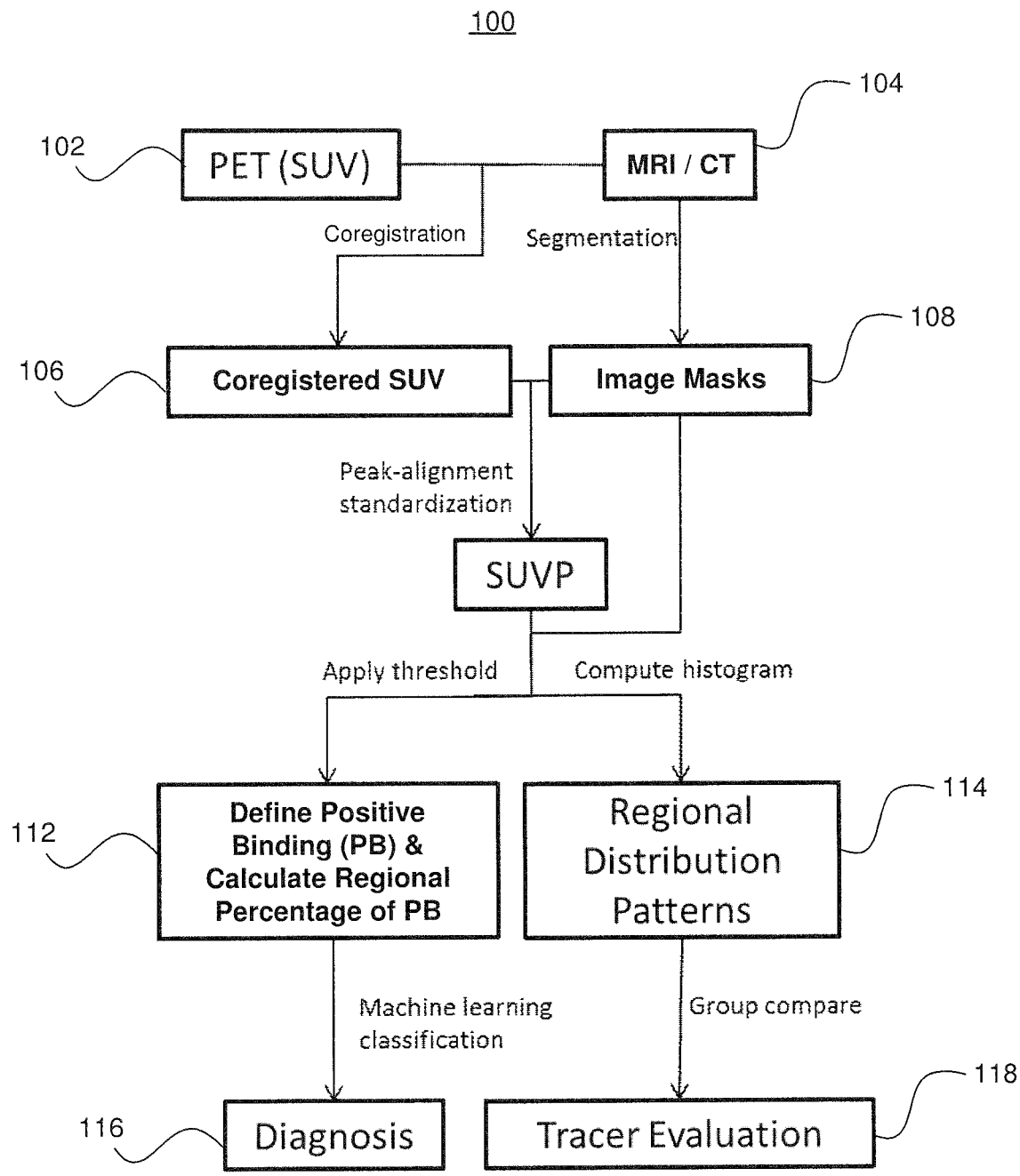
FIG. 1 shows an exemplary embodiment of a method for obtaining and analyzing PET imaging.

In one exemplary embodiment, as shown in FIG. 1, a method 100 for obtaining and analyzing PET imaging is provided. More particularly, the method incorporates the SUVP method, which is mentioned above and further discussed in detail below to provide improve sensitivity and specificity of various PET tracers in diagnosis of AD. However, it is contemplated that the exemplary method 100 shown in FIG. 1 may be useful for any type of PET tracers, including, for example, tau tracers (e.g., $^{18}$F-AV-1451), amyloid tracers, inflammation PET tracers, and/or oncology PET tracers.

In step 102, a PET image may be obtained from a patient to generate raw PET image data. The PET image may be obtained using any suitable PET tracer. The PET tracers may include tau tracers, amyloid tracers, amyloid tracers, inflammation PET tracers, and/or oncology PET tracers. In some embodiments, the PET tracer may be a tracer suitable for use in diagnosis of AD. Suitable PET tracers may include, but is not limited to AV-1451, MK6240, inflammation PET tracers, and/or oncology PET tracer. In one exemplary embodiment, brain AV-1451 and/or THK5351 PET may be used.

In step 104, a magnetic resonance image (MRI) and/or a computed tomography (CT) scan may also be obtained from the same patient. MRI and/or CT scan data that may be used in combination with PET scan data to localize the biologic functionality observed in PET data to anatomical structures obtained using another type of imaging such as, for example, MRI and/or CT images. Specifically, in step 106, the PET data may be co-registered to correspond to anatomical structures represented by an image mask. The image mask may include any suitable form of anatomical images, or may include externally sourced data corresponding to anatomical structures of a predetermine portion of the body, in particular, the brain. For example, any suitable form of anatomical images may be used to generate one or more brain masks 108, or to customize a particular region of interest (ROI) for special interest, such as regions derived from meta-analysis or data-driven parcellation. The anatomical images may include any suitable image data corresponding to the anatomical structure of a particular portion of the patient to be imaged, such as, for example, MRI and/or CT images. The one or more brain masks correlate the PET data to particular locations within images of corresponding anatomical structures. For example, the combination of the PET scan data localized to the anatomical structures observed in MRI and/or CT images provide a way to provide segmentation of the anatomical structure of the scanned area to generate one or more brain masks 108.

In step 110, a SUVP method may be used to analyze regional distribution patterns of the PET data. In particular, the SUVP method normalizes the SUV of PET scans among different subjects using a peak value of the PET image data (M), so that different image histograms may be aligned with each other at each of their peak values so that may be compared to each other. PET tracers were designed to binding specific target, and un-targeted tissue become background and offered a natural reference to adjust the signal intensity. In particular, the peak value (M) may be obtained from a peak of a PET image's SUV histogram. The peak of PET image's SUV histogram may reflect the majority of background signal. More particularly, a sample mode may be used to identify the peak value (M) of a PET image's histogram.

The set of standardized uptake values (with repetition) for all voxels within brain region r and subject s may be represented as SUV(r,s). Each of the values of SUV(r,s) may be normalized using a SUVP method represented as follows:

$$SUVP(r,s)=(SUV(r,s)-M)/S,$$

where M corresponds to a peak of the number of counts of emissions events recorded across all of the voxels of the PET image data, and S corresponds to a spread of all of the different counts of emissions events recorded across all of the voxels of the PET image data. Each subject's SUV image may be normalized and transferred into a standardized SUVP, using the standardized uptake value peak-alignment (SUVP) method described herein.

More particularly, the peak (M) and spread (S) values may be obtained in a number of different ways. For example, the peak (M) and spread (S) values may correspond to any of the following shown below in Table 1.

TABLE 1

| Variables | Measure of | Exemplary Variations |
| --- | --- | --- |
| M | Peak | Mean, media, mode, etc. |
| S | Spread | Standard deviation, inter-quantile range, standard deviation after censorship or winsorizing, etc. |

Figure 4:
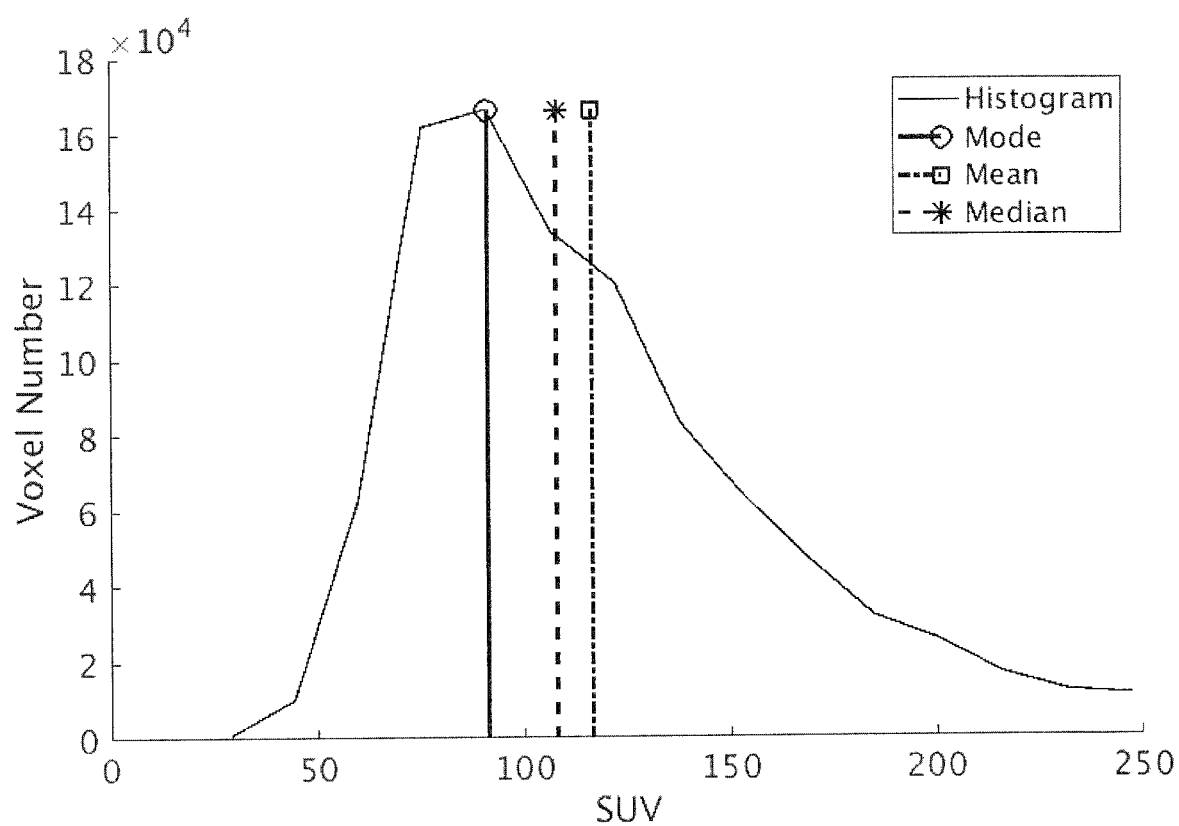

In one particular example, M is the sample mode of rounded SUV(r,s), and S is the standard deviation of SUV (r,s). Furthermore, the peak (M) values, in particular the sample mode of rounded SUV(r,s) may be used as a reference region to normalize raw SUV data using methods similar to SUVR. Although the value of sample mode depends on the number of significant digits after decimal point $N_{sig}$ to which the SUV set was rounded to, data in Example I, discussed further below shows that the sample mode values to be very stable over different choices of $N_{sig}$ (FIG. 4).

The peak-alignment normalization method described above, in particular, the SUVP values, may be useful in: (1) diagnosing an abnormality, such as a disease or condition, e.g., diagnosis of Alzheimer's disease (AD) in a patient, based on a PET image of the patient; and/or (2) development and evaluation of tracers, in particular, new PET tracers, for use in quantitative PET imaging. As described further below, steps 112 and 116 relate to an exemplary use of the SUVPs in diagnosis of patients with AD. In an alternative embodiment, steps 114 and 118 relate to evaluation of tracers in their effectiveness to detect diseases or abnormalities (e.g., AD).

In step 114, a regional distribution pattern of the PET data may be obtained by computing a new PET data histogram using the SUVP normalized data. In particular, the whole brain probability density function $PDF_{wb}(s,r,v)$ can then be obtained by:

$$PDF_{wb}(r,s,v) = N(r,s,v)/N_{ICV}(s),$$

where:

$N(r,s,v)$ is the number of voxels with SUVP(r,s)=v, and $N_{ICV}(s)$ is the total number of intracranial voxels for subject s.

Furthermore, the average whole brain probability density function $\overline{PDF}_{wb}$ over a group of subjects $\{s_i|i=1, 2 \ldots, n\}$ can then be obtained by:

$$\overline{PDF}_{wb}(r,v) = \Sigma_n^{i=1} PDF_{wb}(r,s_i,v)/n.$$

In step 118, the average whole brain probability density function $\overline{PDF}_{wb}$ for the particular groups of subjects can be compared between diseased and normal groups, or between images generated using different tracers, to examine the different tracers' effectiveness of tissue binding and sensitivity to the disease (e.g., Alzheimer's disease (AD)). For example, if tracer A showed more binding in target area, less binding in off-target area, and larger binding differences between AD and normal patients than tracer B, then tracer A will be reported as superior as compared to tracer B in the diagnosis of AD.

In addition, as shown in step 112, a SUVP method may also be used to analyze regional percentages of positive binding in the PET data. Positive binding may be defined based on a predetermined cutoff value. The predetermined cutoff value may be any suitable value that is well above background signal. In some embodiments, the predetermined cutoff value may be manually set by a user. One important advantage of SUVP is that it standardized range of whole brain SUV into a generally fixed range regardless of tracer or disease condition, allowing universal cutoff for different tracers (e.g., 1.5 for all tracers), while SUVR cutoffs are tracer-dependent and varies across different studies (e.g., 1.5 for THK5315 and 1.2 for AV1451). Additionally, as discussed further below in Example I, when SUVP was calculated by using a standard deviation (SD), 1.5 times a SUVP cutoff value is equivalent to 1.5 times SD, which signifies a statistic meaningful way to distinguish and identify positive voxels. The percentage of positive binding (PBP) may be obtained by:

$$PBP = \frac{\text{number of voxels with } SUVP > \text{predetermined cutoff value}}{\text{total number of voxels}} \times 100\%$$

SUVP offers a standard cutoff solution to identify positive voxels, and makes a practical approach to evaluate spread of pathology, instead of relying on regional signal intensity. The PBP of a particular patient for a particular region of interest (ROI) may also be compared to the PBP for the same ROI for the group of subjects $\{s_i|i=1, 2, \ldots, n\}$ to provide a diagnosis (step 116). The ROI may be any particular region of the brain that correlates to the pathology of cognitive decline or AD. In particular, the ROI may be the entire brain or the lateral temporal lobe (LTL).

In another embodiment, the average PBP of a particular diseased (or abnormal) group (e.g., an AD group) for a particular ROI may be compared to the PBP of a group of normal control (NL) subjects. For example, a ratio (R) of PBP may be obtained by:

$$R = (\text{average PBP of diseased or abnormal group})/(\text{average PBP of NL group})$$

If the particular diseased group is an AD group and the R is above a certain predetermined threshold for a particular ROI, the PET tracer may be reported as effective in the detection of AD.

As demonstrated above, the method 100 as described above, in particular the SUVP method avoids using reference region in tradition SUVR method, and avoids errors caused by variations of reference regions' signal. In addition, the SUVP method provides a robust and practical way to evaluate positive binding voxels in PET images.

The SUVP method may be used in evaluating longitudinal changes in PET data. It is believed that the SUVP method may provide improvements to longitudinal PET study, by reducing variability in the data, to allow for better monitoring of disease progression and effect of new treatment.

Those skilled in the art will understand that the exemplary embodiments described herein may be implemented in any number of manners, including as a separate software module, as a combination of hardware and software, etc. For example, the exemplary analysis methods may be embodiment in one or more programs stored in a non-transitory storage medium and containing lines of code that, when compiled, may be executed by at least one of the plurality of processor cores or a separate processor. In some embodiments, a system comprising a plurality of processor cores and a set of instructions executing on the plurality of processor cores may be provided. The set of instructions may be operable to perform the exemplary methods discussed below. The at least one of the plurality of processor cores or a separate processor may be incorporated in or may communicate with any suitable electronic device, for example, a PET imaging device, a mobile computing device, a smart phone, a computing tablet, a computing device, etc.

Figure 7:
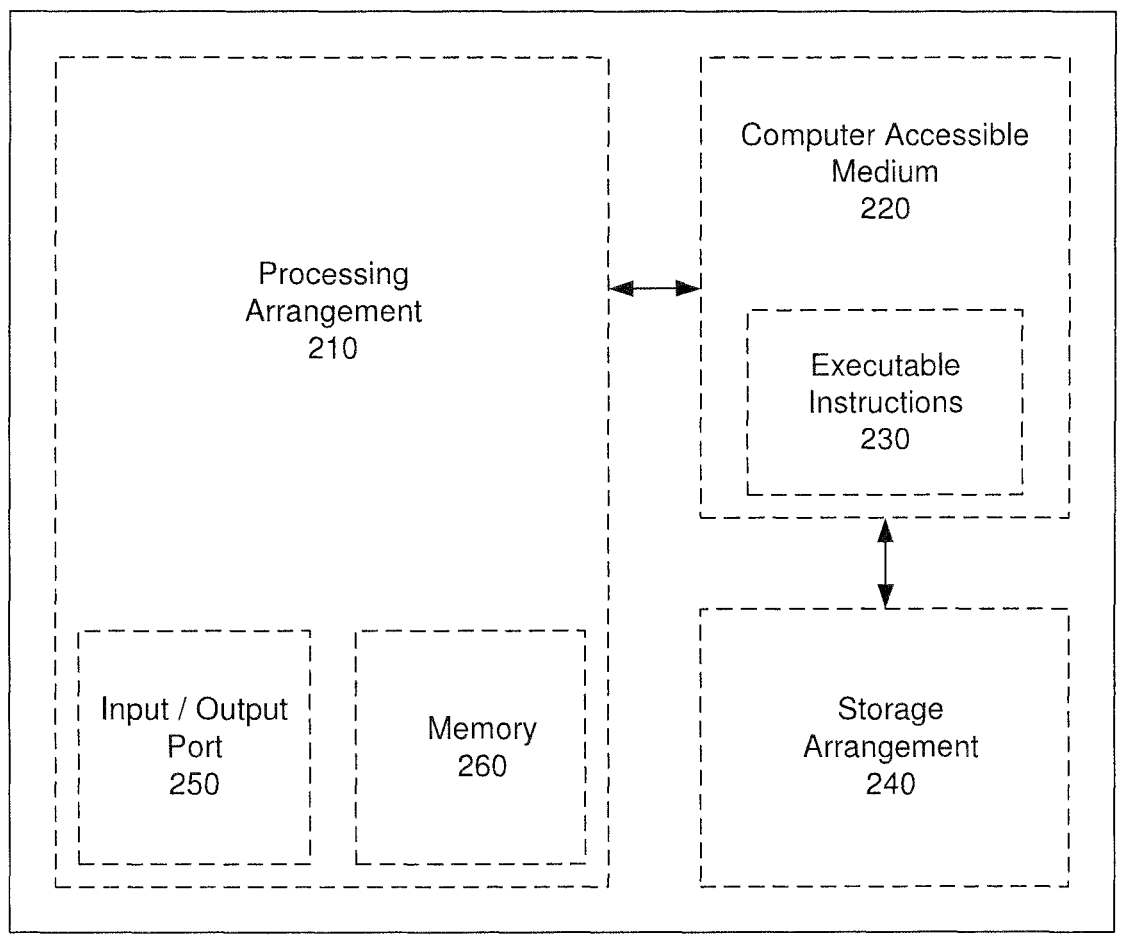
FIG. 7 shows an exemplary computer system for performing a method for obtaining and analyzing PET imaging.

For example, the exemplary methods may be embodied in an exemplary system 200 as shown in FIG. 7. For example, an exemplary method described herein may be performed entirely or in part by a processing arrangement 210. Such processing/computing arrangement 210 may be, e.g., entirely or a part of, or include, but not limited to, a computer/processor that can include, e.g., one or more microprocessors, and use instructions stored on a computer-accessible medium (e.g., RAM, ROM, hard drive, or other storage device). As shown in FIG. 7, e.g., a computer-accessible medium 220 (e.g., as described herein, a storage device such as a hard disk, floppy disk, memory stick, CD-ROM, RAM, ROM, etc., or a collection thereof) can be provided (e.g., in communication with the processing arrangement 210). The computer-accessible medium 220 may be a non-transitory computer-accessible medium. The computer-accessible medium 220 can contain executable instructions 230 thereon. In addition or alternatively, a storage arrangement 240 can be provided separately from the computer-accessible medium 220, which can provide the instructions to the processing arrangement 210 so as to configure the processing arrangement to execute certain exemplary procedures, processes and methods, as described herein, for example. Furthermore, the system 200 may comprise an input/output port 250 to receive data from or to output data to another system or device. For example, the input/output port 250 of an exemplary system 200 of the present invention may be configured to receive raw PET data from a PET imaging device configured to detect radioactive emissions from a patient, following administration of a PET tracer to the patient.

As discussed further below the data of Example 1, shows that SUVP has advantage over SUVR in distinguishing patients from normal controls in brain Tau PET image. The SUVP method described herein has potential to replace SUVR as a new standard of PET image normalization method, and potentially as a part of key method for computer-assisted diagnosis. Better characterizing of these tau PET tracers allows better design of clinical studies and development of new treatments, as well as progress monitoring.

EXAMPLE

Example I

A total of 50 PET scans were analyzed, including Alzheimer's disease (AD) patients and normal control (NL) subjects, from two Tau PET tracers AV1451 and THK5351. Off-target bindings were found in cerebellum, a conventional reference region for Standardized Uptake Value Ratios (SUVR), and other regions like cerebral WM. The SUVP method showed advantage over SUVR in AD-NL classification. Using the method 100 described above, decreased MAO-B binding in frontal and basal ganglia in AD was observed.

Method and Material

Clinical PET Study Participants:

Subjects come from two sources. 18 subjects (9 AD patients, and 9 healthy elderly study participants) underwent $^{18}$F-THK5351 PET scans from the memory clinic of Tohoku University Hospital. $^{18}$F-AV-1451 scans were obtained from the ADNI (Alzheimer's Disease Neuroimaging Initiative) database (adni.loni.usc.edu). 32 Subjects (20 NL and 12 AD) with $^{18}$F-AV-1451 were selected from ADNI, that were matched to the age and MMSE in participants of the THK5351 group. Participant demographic data are shown in Table 2.

TABLE 2

| | AV-1451 NL | AV-1451 AD | THK5351 NL | THK5351 AD |
|---|---|---|---|---|
| N | 20 | 12 | 9 | 9 |
| Age (range) | 73 (68, 82) | 78 (60, 90) | 73 (61, 90) | 76 (58, 88) |
| Female % | 9 (45) | 6 (50) | 2 (22) | 3 (33) |
| MMSE | 29 (28, 30) | 21 (14, 25) | 29 (27, 30) | 20 (18, 25) |

Abbreviations: AD, Alzheimer's disease; NL, normal control; MMSE, Mini-Mental State Examination.

An ethics committee approved written informed consent was obtained from all participants or the legal care takers. The AD diagnoses were made at a consensus conference according to the National Institute of Neurological and Communicative Disorders and Stroke/AD and Related Disorders Association criteria. All participants received a standardized neuropsychological and clinical assessments, a high resolution T1 weighted MRI, and tau PET exams PET and MRI Image Acquisition

1. $^{18}$F-THK5351

PET imaging was performed using an Eminence STARGATE PET scanner (Shimadzu, Kyoto, Japan). After intravenous injection of $^{18}$F-THK5351 (185 MBq), dynamic PET images were obtained for 60 min. acquisition matrix is 128×128×79 and voxels size is 2×2×2.6 mm. $^{18}$F-THK5351 was synthesized. MRI was performed on all participants. T1 weighted MR images were obtained using a SIGNA 1.5-Tesla machine (General Electric, Milwaukee, Wis.). In T1-weighted MRI, a 3D volumetric acquisition of a T1-weighted gradient echo sequence produced a gapless series of thin axial sections by using a vascular TOF SPGR sequence (echo time/repetition time, 2.4/50 ms; flip angle, 45°; acquisition matrix, 256×256; 1 excitation; field of view, 22 cm; slice thickness, 2.0 mm).

2. $^{18}$F-AV-1451

AV-1451 data were downloaded from ADNI with series description "AV1451 Coreg, Avg, Std Img and Vox Siz, Uniform Resolution". An intravenous injection of 10 mCi $^{18}$F-AV-1451 (370 MBq) is followed by a saline flush. At approximately 75 minutes following injection, a continuous 30-minute brain scan (6 frames of 5-minute duration) was performed after a CT or transmission scan for attenuation correction. PET imaging was performed using GEMINI TF TOF 16 (Philips Medical Systems), with 6 frames; acquisition matrix 128×128×90; pixel spacing 2×2 mm; slice thickness 2 mm.

The corresponding T1 weighted MRI data were downloaded from ADNI. The MRI data were acquired with TrioTim 3T scanner (Siemens); 3D sagittal acquisition; FA 9°; acquisition matrix 240×256×176; spacing 1.0×1.0 mm; slice thickness=1.2 mm; TE=2.98 ms; TI=900 ms; TR=2300 ms.

MRI Regional Segmentation:

Using Free-Surfer (V. 5.1, http://surfer.nmr.mgh.harvard.edu) ROI's were determined for the cerebral gray and white matter, the cerebellar hemisphere gray matter, caudate nuclear, thalamus, ponds and subcortical regions (including frontal, parietal, occipital, medial temporal cortex and lateral temporal lobe). MRI T1 images were coregistered to the mean PET images for each participant by using statistical parametric-mapping software (SPM12; Wellcome Department of Imaging Neuroscience, UCL, London, UK).

Estimations of PET Tracer Binding:

Standardized uptake value (SUV) images were obtained by normalizing tissue radioactivity concentration by injected dose and bodyweight. Estimates of tau deposition were determined for THK53151 with the 40-60 min SUV and for AV1451 with for the 80-100 min SUV. Standard SUVR was generated by using cerebellar cortex as reference. To control the variation of SUVR measures in THK5351 and AV1451 PET caused by the off-target binding in reference region, each subject's SUV images were first transferred into standardized SUVP images, using the Peak-alignment method (as described above). In order to compare the regional SUV distribution patterns on group level, the whole brain probability density function ($PDF_{wb}$) of SUVP were computed for each subject by normalizing the histograms of a subject's SUVP with the total number of intracranial voxels of that subject. Finally, the group average whole brain probability density function ($\overline{PDF}_{wb}$) were computed by averaging the individual subjects' $\overline{PDF}_{wb}$ within 4 compare groups (2 tracers×2 conditions). One important advantage of SUVP over SUVR is that the Peak-alignment method standardized the range of whole brain SUV (marked in FIG. 2) into [−3,3] approximately, regardless of tracer or disease condition, thus allowing universal cutoff for different tracers, while SUVR cutoffs are tracer-dependent (e.g. 1.5 for THK and 1.19 for AV1451). Here, 1.5 is used for SUVP cutoff, representing 1.5 times std from whole brain mode. The positive binding percentage: PBP=(number of positive bring voxels)/(total number of voxels), are computed for both SUVP and SUVR in different brain tissues.

Statistical Analyses:

All statistical analyses were conducted with SPSS (Version 23, IBM Inc.)

1. Tissue Classification:

Within each tracer, the mean SUVR, PBP of SUVR and PBP of SUVP were compared between AD and NL subjects. ROIs of comparison includes Cerebral GM/WM, Basal ganglia areas for all measurements, and Cerebellum GM/WM for SUVP measurements only (Cerebellum SUVR are close to 1 by definition). Nonparametric Mann-Whitney U test was used for THK5351 data, since the data did not pass normality tests. Two-sample t-test was used for AV1451 data, since the data passed normality tests.

2. Regional Tracer Binding:

To find the most prominent cortical region in AD, the mean SUVR and PBP (SUVP) in temporal cortex were compared against frontal cortex, parietal cortex, and occipital cortex, with pairwise t-test.

3. Diagnostic Accuracy:

To compare the classification accuracy of AD and NL using mean SUVR and PBP (SUVR and SUVP), the ROC curve was computed and the area under curve (AUC) was computed.

Results

1. SUVR in Tissue Classification and Regional Tracer Binding

The SUVR maps of four typical subjects (one from each tracer/condition) are obtained. As expected, Higher global cerebral gray matter (GM) binding was found in AD comparing to NL for both THK5351 and AV-1451 in SUVR (U=64, p<0.05; F=5.8 p<0.05. respectively) (Table 3 showing tissue classification (SUVR)).

TABLE 3

|  | THK5351 | | AV-1451 | |
| --- | --- | --- | --- | --- |
|  | NL (n = 9) | AD (n = 9) | NL (n = 20) | AD (n = 12) |
| Cerebral GM | 1.39(.20) | 1.55(.16)[+] | 1.09(.09) | 1.24(.25)[+] |
| Cerebral WM | 1.56(.20) | 1.78(.14)[+] | 1.18(.09) | 1.27(.18) |
| Basal ganglia | 2.64(.31) | 2.62(.26) | 1.30(.09) | 1.30(.10) |

Data present as mean (SD).
[+]Significant higher in AD comparing to NL (p < 0.05)

THK5351 also showed higher cerebral white matter bindings in AD (U=67, p<0.05). The most prominent cortical region in AD is temporal cortex, comparing to frontal cortex (t(8)=18.3 p<0.01), parietal cortex (t(8)=8.8 p<0.01) and occipital cortex(t(8)=11.4 p<0.01) in THK5351. Similar finding was observed in AV-1451, where temporal cortex SUVR is higher than frontal cortex (t(11)=5.9 p<0.01), parietal cortex (t(11)=5.8 p<0.01) and occipital cortex(t(11)=3.7 p<0.01) (Table 4 shows regional tracer binding (SUVR)).

TABLE 4

|  | THK5351 | | AV-1451 | |
| --- | --- | --- | --- | --- |
|  | NL (n = 9) | AD (n = 9) | NL (n = 20) | AD (n = 12) |
| Temporal cortex | 1.57(.21) | 1.88(.22)*[+] | 1.18(.16) | 1.41(.35)*[+] |
| Frontal cortex | 1.32(.20) | 1.38(.18) | 1.06(.07) | 1.18(.23) |
| Parietal cortex | 1.30(.24) | 1.46(.12) | 1.07(.10) | 1.25(.30) |
| Occipital cortex | 1.22(.13) | 1.42(.16)[+] | 1.09(.09) | 1.17(.13) |

Data present as mean (SD).
*Significant higher than other regions (p < 0.01).
[+]Significant different from NL after Bonferroni correction.

THK5351 showed higher binding in temporal cortex (U=73 p<0.01) and occipital cortex (U=70 p<0.01) in AD comparing to NL. AV-1451 showed higher binding in temporal cortex (F=8.14 p<0.01) in AD comparing to NL. Cerebral WM showed higher tracer retention than Cerebral GM in both tracers (For AV-1451, $WM_{SUVR}$=1.21(0.13), $GM_{SUVR}$=1.15(0.18), t(31)=5.4 p<0.01); For THK5351, $WM_{SUVR}$=1.67(0.20), $GM_{SUVR}$=1.47(0.19), t(17)=10.4 p<0.01). Off-target binding was observed on image in cerebral white matter and basal ganglia region in both THK5351 and AV-1451, and cerebellum in AV1451, a conventional reference region.

Figure 2:
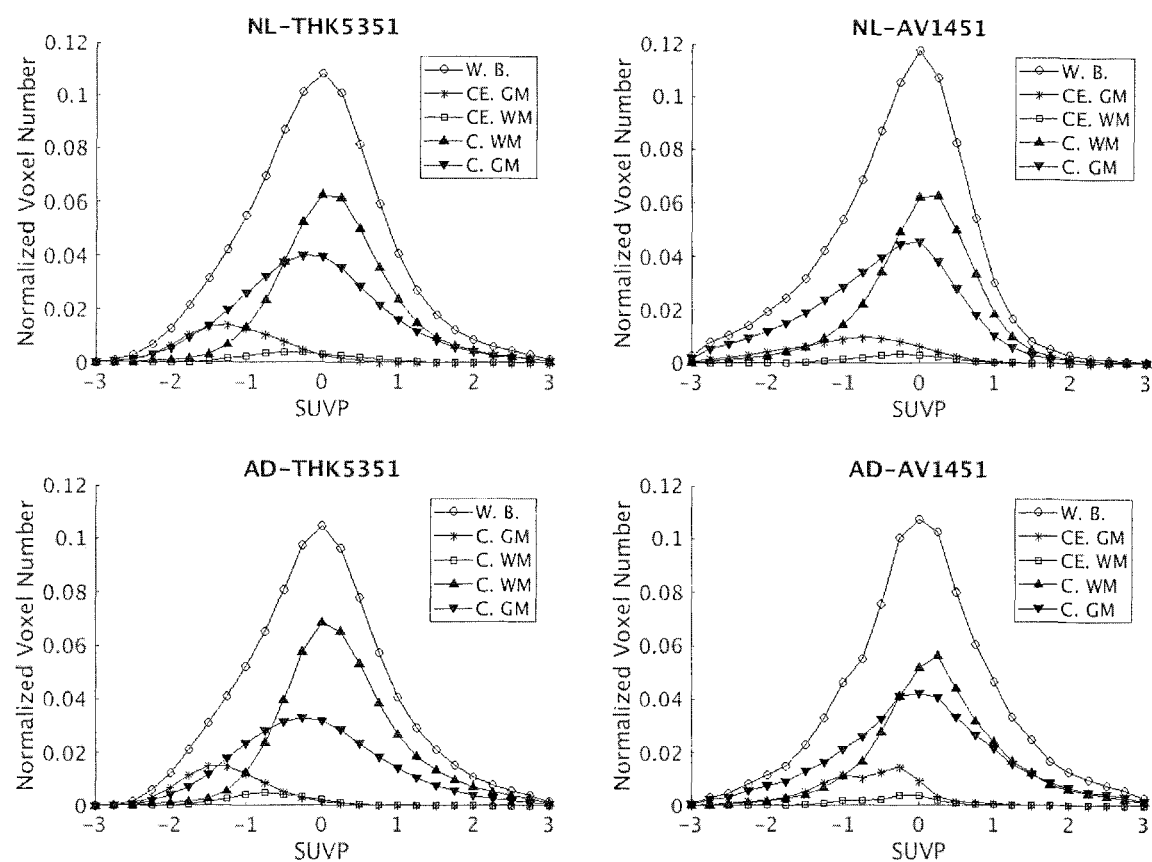
FIGS. 2-6 show experimental data as discussed further below in Example I.

FIG. 2 shows a mean SUVP histograms of two tracers- and two condition-groups, displayed in a 2×2 layout. Up row=NL; bottom row=AD; left column=THK5351; right column=AV1451. In each subplot, X axis is SUVP value; Y axis is the voxel counting divided by total intracranial voxel numbers. The distance of peaks between cerebellar GM and whole brain is shorter in AD comparing to NL for AV1451. But shorter in NL comparing to AD for THK5351.

2. SUVP in Tissue Classification and Regional Tracer Binding

To reduce the bias of SUVR measures in caused by the off-target binding in reference region. We developed the SUVP method by standardizing the peak and span (or spread) of regional SUV distribution. The tracers' SUVP distribution patterns of same four subjects are obtained. Compared to SUVR maps, the SUVP maps enhanced the positive binding voxel clusters, as well as revealed the off-target binging that was invisible on SUVR maps.

The mean SUVP histograms for the 2×2 compare groups (AD vs NL, THK5351 vs AV1451) are shown in FIG. 2. The AD-NL ratio R as defined as (average PBP of AD group)/(average PBP of NL group) and group difference P-values are provided in Table 5.

TABLE 5

|  | SUVR | SUVP |
| --- | --- | --- |
| THK5351 | R = 1.2747 P = 0.050 | R = 3.1248 P = 0.001 |
| AV1451 | R = 1.3258 P = 0.049 | R = 4.4004 P = 0.012 |

In all four groups, the peak values of cerebral WM curves are larger than cerebral GM curves, confirming the WM off-target binding found in SUVR results. In SUVP scale the group difference of brain biding is stronger for AV-1451 than THK-5351 by visual observation. As expected the peak values of cerebellum GM curves are low in all four groups, reflecting the low binding in that area. However, difference of peak values as well as distribution patterns can still be seen between AD and NL for both tracers, indicating the potential bias of using whole cerebellum GM as reference region in SUVR. The mean SUVP in cerebellum GM, although low as expected, showed opposite directions of differences in two tracers. (THK5351: AD<NL GM SUVP is −1.21(0.28) for NL and −1.24(0.24) for AD (p>0.05) AD showed a 2.5% decrease comparing to NL; AV1451: AD>NL the cerebellar GM SUVP is −1.00(0.45) for NL and −0.73(0.43) for AD, AD showed a 37% increase comparing to NL and is a trend in group test (F=2.9 p=0.09), again suggested the potential risk of using cerebellum as reference in SUVR.

Higher WM peaks was observed comparing to GM peaks on histograms, cerebellar gray matter also showed higher signal retention difference between NL and AD, especially in AV1451 (FIG. 2). The off-target binding in cerebellum was observed in PET image. It raised the question of using cerebellum as the reference region for standardizing SUV, as variances of cerebellum causes the SUVR to be subject to over or under estimation of SUV.

As expected, AV-1451 showed higher binding in GM (F=8.7 p<0.01) and WM (F=7.1 p=0.01) for AD comparing to NL. THK5351 also showed higher GM binding for AD comparing to NL, but only a trend (U=67 p=0.07). Interestingly, higher tracer retention in Basal ganglia (U=4 p<0.01) and Cerebellar WM (U=9 p<0.01) was found in NL comparing to AD in THK5351. (Table 6 showing tissue classification in PBP of SUVP).

TABLE 6

|  | THK5351 | | AV-1451 | |
| --- | --- | --- | --- | --- |
|  | NL (n = 9) | AD (n = 9) | NL (n = 20) | AD (n = 12) |
| Cerebral GM | 3.81(2.19) | 5.56(1.47) | 1.85(3.24) | 9.4(10.83)[+] |

TABLE 6-continued

|  | THK5351 | | AV-1451 | |
| --- | --- | --- | --- | --- |
|  | NL (n = 9) | AD (n = 9) | NL (n = 20) | AD (n = 12) |
| Cerebral WM | 7.06(1.55) | 8.70(3.24) | 2.65(3.64) | 7.86(7.44)[+] |
| Basal ganglia | 81.24(8.55)[++] | 61.93(7.25) | 28.14(11.42) | 18.55(12.28) |
| Cerebellar GM | .10(.14) | .07(.10) | .83(1.45) | .90(1.46) |

Data present as mean (SD).
[+]Significant higher in AD comparing to NL (p < 0.01);
[++]Significant higher in NL comparing to AD (p < 0.01), after Bonferroni correction.

Same as in SUVR, the most prominent cortical region in AD in terms of PBP is also temporal cortex, comparing to frontal cortex (t(8)=12.03 p<0.01), parietal cortex (t(8)=8.21 p<0.01) and occipital cortex(t(8)=10.77 p<0.01) in THK5351. Similar finding was observed in AV-1451. Temporal cortex SUVR is higher than frontal cortex (t(11)=3.86 p<0.01), parietal cortex (t(11)=4.16 p<0.01) and occipital cortex(t(11)=3.22 p<0.01) (Table 7 shows regional tracer binding PBP of SUVP).

TABLE 7

|  | THK5351 | | AV-1451 | |
| --- | --- | --- | --- | --- |
|  | NL (n = 9) | AD (n = 9) | NL (n = 20) | AD (n = 12) |
| Temporal cortex | 6.93(4.78) | 17.94(5.15)*[+] | 5.44(11.10) | 20.72(20.48)*[+] |
| Frontal cortex | 2.37(1.25)[+] | 1.25(0.86) | 0.78(1.43) | 5.32(7.70) |
| Partial cortex | 0.17(0.21) | 2.16(3.33)[+] | 0.95(3.21) | 10.2(15.2)[+] |
| Occipital cortex | 0.05(0.09) | 1.73(2.79) | 0.54(1.58) | 5.59(8.23)[+] |

Data present as mean (SD).
*Significant higher than other regions (p < 0.01).
[++]trend significance.
[+]Significant from NL after Bonferroni correction.

THK5351 showed higher binding in temporal cortex (U=75 p<0.01) and parietal cortex (U=73 p<0.01) in AD comparing to NL. Interestingly, frontal cortex shower higher tracer retention in NL comparing to AD with a trend (U=18 p=0.05). AV-1451 showed higher binding in temporal cortex (F=8.14 p<0.01), parietal cortex (F=6.99 p=0.01), and occipital cortex (F=7.23 p=0.01) in AD comparing to NL.

Off-target binding were also observed in non-brain regions such as retina. Off-target binding was observed on image in cerebral white matter and basal ganglia region in both THK5351 and AV-1451.

3. SUVR and SUVP in Diagnostic Accuracy

To compare the AD-NL separation capability of regional SUVP and SUVR, we computed between-group ratio of group average PBP ($R=\overline{PBP}_{AD}/\overline{PBP}_{NL}$) in temporal lobe, where both tracers' SUVR results showed prominent regional binding (Tables 4 and 7). We also computed the diagnostic accuracy in terms of AUC, as specified in Method section. For both tracers, SUVP PBP showed higher between-group ratio and diagnostic accuracy than SUVR PBP and conventional SUVR mean (Table 8 shows diagnostic accuracy and between-group ratio of PBP in temporal lobe), indicating superior separation capability of SUVP method in temporal cortex. The AD-NL ratio obtained using (average PBP of AD group)/(average PBP of NL group).

TABLE 8

| Tracer | | SUVR Mean | SUVR PBP | SUVP PBP |
|---|---|---|---|---|
| Diagnostic Accuracy (AUC) | THK5351 | 0.89 | 0.78 | 0.96 |
| | AV1451 | 0.75 | 0.73 | 0.86 |
| AD-NL ratio (R) | THK5351 | 1.18 | 1.25 | 2.39 |
| | AV1451 | 1.17 | 1.3 | 3.69 |

Figure 3:
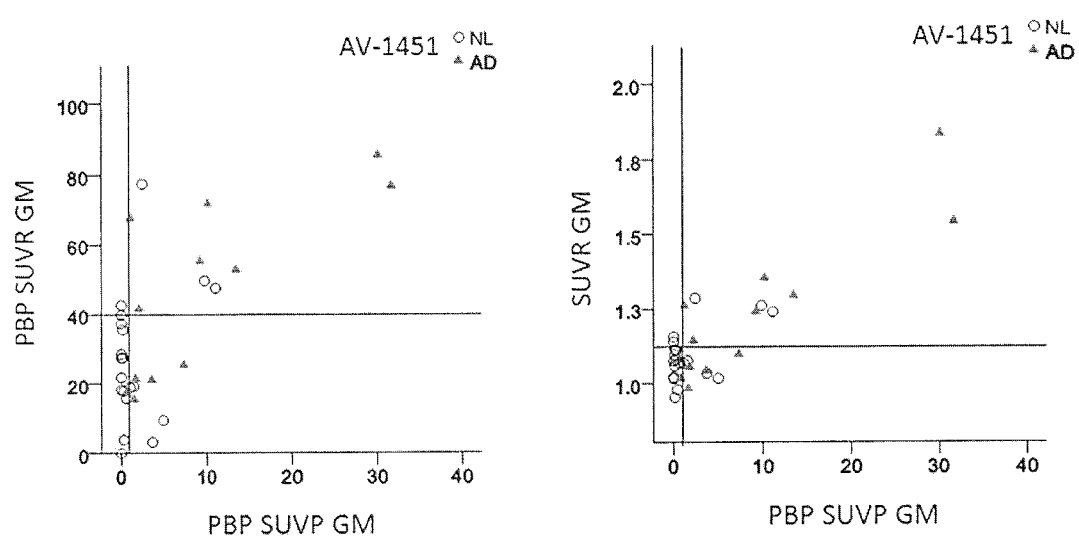

To compare the AD-NL separation capability of global SUVP and SUVR, we tested the diagnostic accuracy of in AV-1451 subjects with the PBP (SUVP and SUVR) and mean SUVR in cerebral GM (FIG. 3). SUVP PBP (AUC=0.85) is superior in predication accuracy than SUVR PBP (AUC=0.71) and conventional mean SUVR AUC=65%. In THK5351 none of the three features showed any significant between-group differences. This is probably caused by the MAO-B off-target binding in THK5351—elaborated in Discussion section below.

Discussion

1. Binding Distribution Patterns

THK5351 and AV-1451 both can reflect tau pathology in AD brains. However, off-target binding become a common issue and even affected cerebellum cortex, the conventional reference region. "Off-target" binding was detected in Basal ganglia for both THK5351 and AV-1451, in choroidal plexus and substantia nigra for AV-1451, and in ponds and Amygdala for THK5351. Moreover, off-target binding affected cerebellum. In both tracers. the SUVR (cerebellum as reference) differences between AD and NL are partially caused by this off-target binding rather than real tau pathology differences. In SUVR scale, off-target binding limited the power of tau tracers, especially AV-1451, in disease diagnosis.

MAO-B off-target binding in THK5351 was observed. SUVP data showed decreased tracer retention in AD group in frontal lobe and basal ganglia region comparing to NL. Decreased off-target binding in AD for THK5351, which indicates MAO-B level reduced in AD, was observed. It may also explain why global measure of GM binding lost significance in THK5351 by using SUVP method. On the other side, the temporal lobe tau measure was less affect by the off-target binding, and showed significant group difference. AV-1451 showed cerebellum SUVP PNP group difference. AD subjects showed 37% higher than NL. It limited its power of tau tracers in disease diagnosis. In this Example, SUVP PNP increased the diagnosis accuracy to 85%, comparing to SUVR PNP 71% and conventional SUVR 65% in global cortex tau measure.

2. Compare of SUVR and SUVP

Distributions of individual subjects' SUV vary in peaks and spans (or spreads) because of the scanner and subject differences. Standardization method is necessary for investigating PET SUV of different subjects, from different centers. The SUVR method is subject to bias because the variation of reference regions' signal (SUV) especially in different study groups (such as Alzheimer's patient and normal control, causing underestimation or overestimation of real group difference. The SUVP method uses the peak of PET image's histogram to evaluate the signal intensity. Tau PET tracers were designed to bind hyperphosphorylated tau (PHF-tau), and un-targeted tissue become background and offered a natural reference to adjust the signal intensity. The peak of PET image's histogram reflects the majority of background signal. Instead of using reference region, SUVP picks un-targeted tissue as contrast. The peak-alignment algorithm provides in AD-NL separation, as well as two other major improvements:

1. Instead of using the scalar value of regional average SUVR, it is recommended the standardized probability density function of SUV, which provides richer features for the binding and avoids potential binding issues in the reference region, be used.

2. The SUVP method used in Example I uses sample mode, instead of mean, in the "z-score style" standardization. For the single-peak, slightly-skewed distribution (confirmed by K-S and A-D normality tests) of the whole brain SUV, sample mode captures the "baseline" better than mean or median (shown in FIG. 4). FIG. 4 shows Subj 4521, 15 bins compare of mode, mean and median. There is also a biological argument for choosing mode: when radiologists are reading the PET scans, their perception of the "image brightness" is not reflecting the mean pixel value of the image. Rather, the perception is based on the value of the majority pixels, i.e. the most frequent value. Likewise, when radiologists adjust the intensity window of different PET scans to a same recognizable range for diagnoses, they are actually doing manually standardizing the image mode, not mean.

Figure 5:
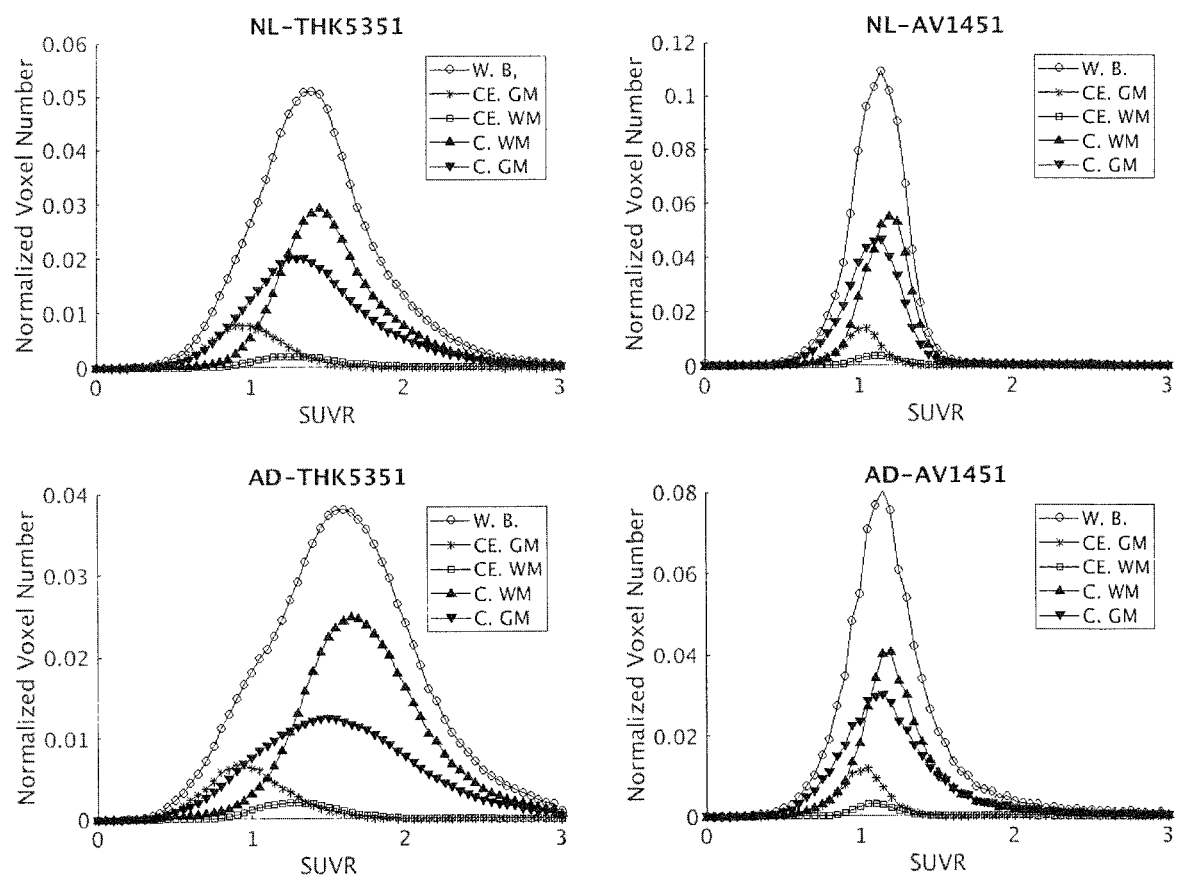

As mentioned in the result section, a main advantage of SUVP is the standardization of SUV range. For the same subjects, the group mean histograms of SUVR (counting normalized by total intracranial voxel numbers) are shown in FIG. 5. FIG. 5 shows mean SUVR histograms of two tracer- and two condition-groups, displayed in a 2×2 layout. Up row=NL; bottom row=AD; left column=THK5351; right column=AV1451. In each subplot, X axis is SUVR value; Y axis is the voxel counting divided by total intracranial voxel number. Compared with FIG. 2, large variation of data ranges can be observed between two tracers, making it challenge to compare the distribution patterns across the tracers.

Figure 6:
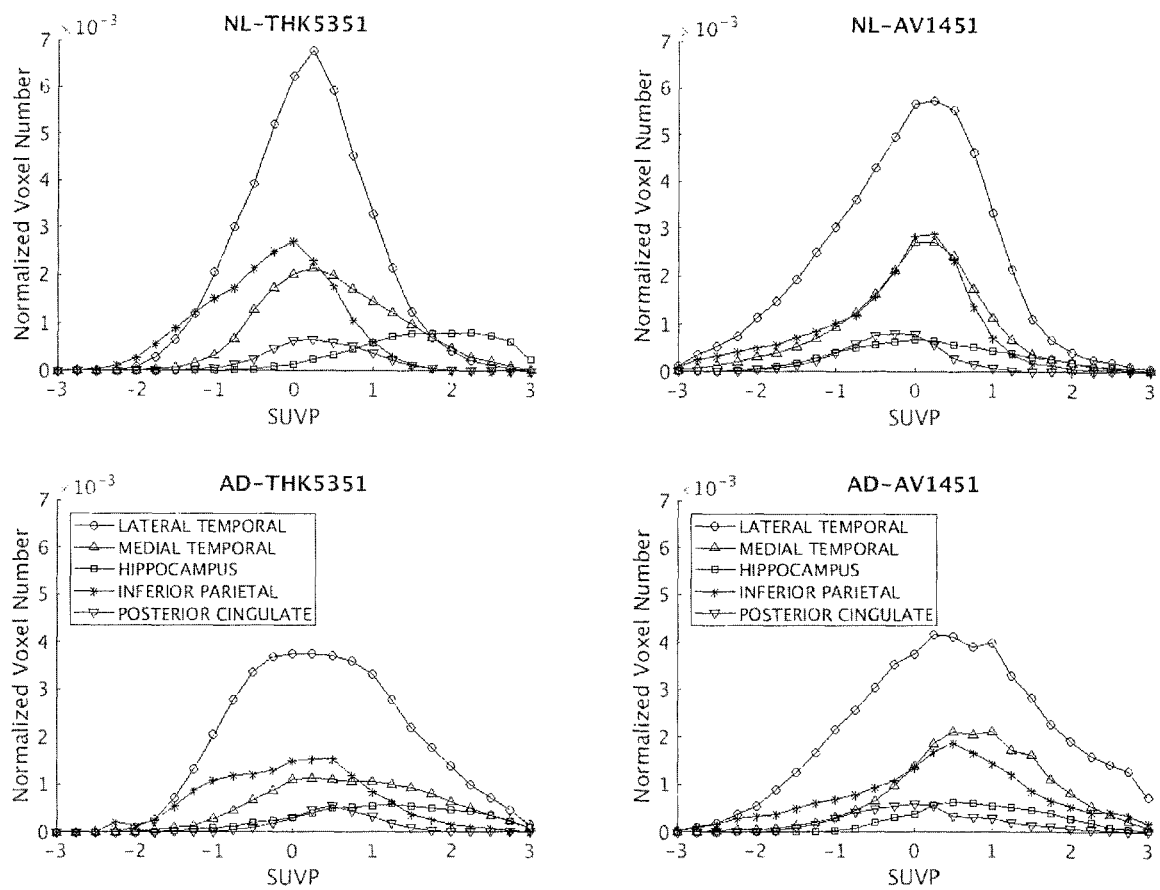

SUVP method can also be used to analyze target binding areas. The group mean SUVP curves for target binding areas defined in Table 9, which lists ROI definitions, are shown in FIG. 6.

TABLE 9

| ROI | Type | Freesurfer label values |
|---|---|---|
| WHOLE BRAIN | Brain tissue | 8 + 47 + 7 + 46 + 2 + 41 + 1000~2035 |
| CEREBELLUM GM | Brain tissue | 8 + 47 |
| CEREBELLUM WM | Brain tissue | 7 + 46 |
| CEREBRAL WM | Brain tissue | 2 + 41 |
| CEREBRAL GM | Brain tissue | 1000~2035 |
| BASAL GANGLIA | Brain tissue | 10 + 11 + 12 + 13 + 28 + 49 + 50 + 51 + 52 + 60 |
| TEMPORAL LOBE | Binding area | 1009 + 1015 + 1030 + 2009 + 2015 + 2030 + 2006 + 2007 + 2016 + 1006 + 1007 + 101 |
| HIPPOCAMPUS | Binding area | 17 + 53 |
| INFERIOR PARIETAL | Binding area | 1008 + 2008 |
| POSTERIOR CINGULATE | Binding area | 1023 + 2023 |

TABLE 9-continued

| ROI | Type | Freesurfer label values |
|---|---|---|
| FRONTAL LOBE | Binding area | 1032 + 2032 |
| OCCIPITAL LOBE | Binding area | 1011 + 2011 + 1013 + 2013 + 1005 + 2005 + 1021 + 2021 |

CONCLUSION

In Example 1, the regional Tau binding patterns of two PET tracers in two groups of subjects were compared. Off-target binding in reference region for both tracers was observed, which indicates potential bias in SUVR.

The SUVP method was developed to provide robust and unbiased estimation of Tau binding, by controlling the peak and span (or spread) of regional SUV histograms. Example I shows that SUVP has advantage over traditional SUVR in detecting AD from NL subjects. SUVP offered a standard unbiased cutoff solution to identify positive voxels, and made a practical approach to evaluate spread of pathology, both of which are challenging in traditional SUVR method.

Example II

Example II, as discussed below, provides an exemplary embodiment comparing tau PET uptake quantification methods based on a 18F-AV-1451 tracer. Quantitative measurement of tau bindings from PET tracers (such as AV1451) is crucial in the PET-based study of tauopathies (such as Alzheimer's). The standardized uptake value ratio (SUVR) method has been challenged by the off-target binding in reference region. An unbiased tau binding quantification may be achieved via several different methods, including the Parametric Estimate of Reference Signal Intensity (PERSI) method by Avid Radiopharmaceutical and standardized uptake value peak-alignment (SUVP) method. In Example II, we compared the sensitivity of SUVR, PERSI and SUVP methods on the same PET dataset, in both global and local regions.

Methods:

Using SUVR, PERSI, and SUVP, we evaluated the global and regional tau binding of 18F-AV-1451 on 64 subjects, with 42 cognitively normal (NL) and 22 Alzheimer's disease (AD), and compared the group differences of tau binding under the three different methods. Cerebral cortex was used as ROI for global binding test. The average SUVP value in ROIs is computed by averaging all positive SUVP values (SUVP>0) within the ROI, and positive binding percentage (PBP) for SUVP is defined as the ratio of voxel number with SUVP>1.5 over the total voxel number within the ROI.

Figure 8:
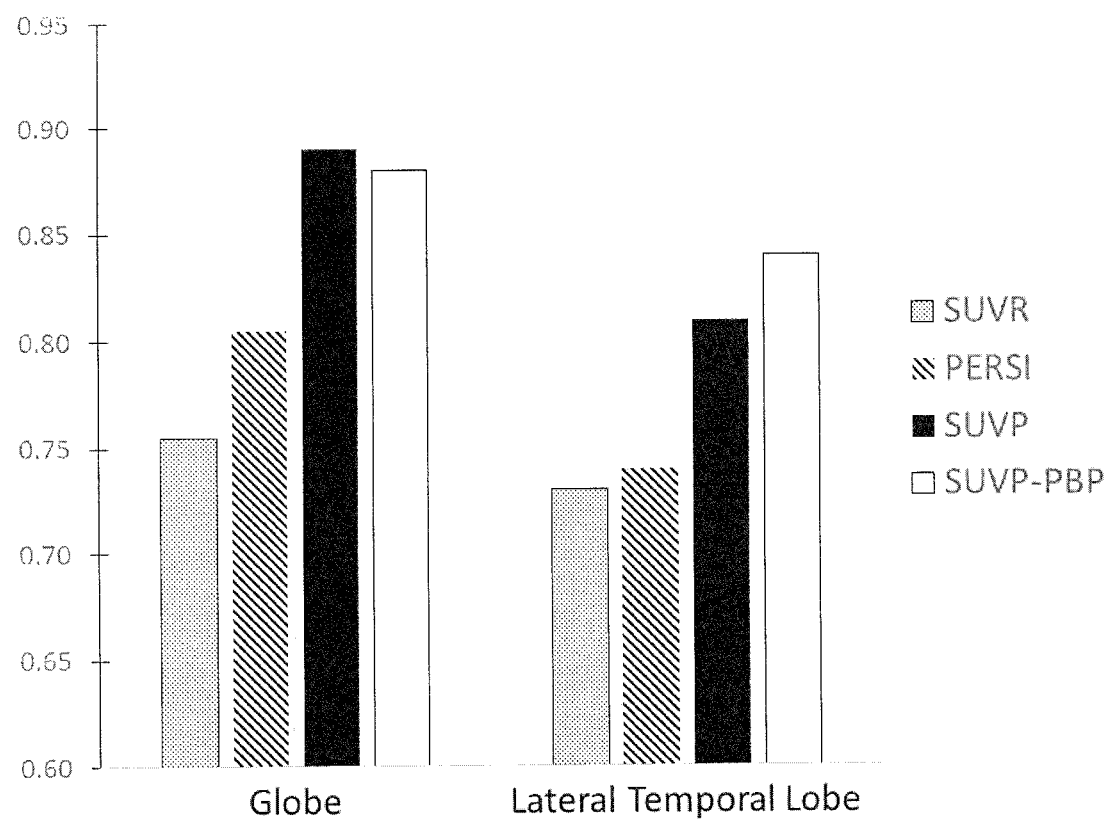
FIG. 8 shows experimental data as discussed further below in Example II.

Results:

AD subjects showed significantly higher tau binding than cognitively normal NL subjects, with SUVR, PERSI and SUVP. For global and lateral temporal lobe binding, SUVP showed higher sensitivity than PERSI, and PERSI higher than SUVR. The classification accuracy between AD and NL are shown in FIG. 8 in terms of AUC of ROC. As shown in FIG. 8, the data obtained using SUVP are represented two ways: as a percentage of positive binding observed using the SUVP method (SUVP-PBP) and as an average SUVP in ROIs. The bar chart of FIG. 8 shows the global and lateral temporal lobe binding as detected by SUVR, PERSI, SUVP, and SUVP-PBP in that order. The results show that SUVP-PBP and SUVP provide greater AD classification accuracy than PERSI and SUVR methods.

Conclusion:

All three methods can pick up the tau binding group difference between AD and NL. By avoiding the bias from off-target binding, PERSI and SUVP showed improvement of disease senility in measuring global binding and local binding of late Braak Stage regions. However, both PERSI and SUVP results indicated that the tau pathology may already affect early Braak Stage regions in "clinically normal ageing" subjects.

The invention described and claimed herein is not to be limited in scope by the specific embodiments herein disclosed since these embodiments are intended as illustrations of several aspects of this invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All publications cited herein are incorporated by reference in their entirety.

What is claimed is:

1. A method for analyzing Positron Emission Tomography (PET) image data comprising:

localizing the PET data with at least one image mask to generate localized PET data, wherein the PET data is co-registered to correspond to anatomical structures represented by the image mask;

generating a set of image intensity values (Ps) based on the localized PET data for voxels within a selected region of interest (ROI), each of the image intensity values corresponding to an intensity of the PET data for a corresponding one of the voxels;

normalizing the set of image intensity values (Ps) by generating a set of normalized values (Ns) where each corresponding N for each P is obtained using the formula:

$$N=(P-M)/S,$$

wherein

M corresponds to a peak value for the set of image intensity values (Ps), and

S corresponds to a spread for the set of image intensity values (Ps); and generating a normalized image based on the set of normalized values (Ns).

2. The method of claim 1, further comprising fitting a Gaussian curve to a histogram of the set of image intensity values (Ps), wherein M is a mean of the fitted Gaussian curve, and S is a standard deviation of the fitted Gaussian curve.

3. The method of claim 1, wherein the ROI corresponds to a predetermined portion of a patient's body.

4. The method of claim 3, wherein the predetermined portion is an entire brain.

5. The method of claim 1, wherein the image intensity values (Ps) are standardized uptake values (SUVs).

6. The method of claim 5, wherein M is a peak of the set of SUVs, and S is a spread the SUVs.

7. The method of claim 1, wherein the image mask comprises anatomical image data.

8. A non-transitory computer-readable storage medium including a set of instructions executable by a processor, the set of instructions, when executed by the processor, causing the processor to perform steps of claim 1.

9. The non-transitory computer-readable storage medium of claim 8, wherein the set of instruction further comprises instructions, when executed by the processor, causes the processor to control an imaging device configured to detect radioactive emissions from a patient for a predetermined period of time, and causes the processor to generate the PET data based on the radioactive emissions detected by the device.

10. A Positron Emission Tomography (PET) image system, comprising:
- an imaging device configured to detect radioactive emissions from a patient for a predetermined period of time, the device further configured to generate PET data based on the detected radioactive emissions;
- a memory storage device configured to store the PET data; and
- a processing arrangement configured to localize the PET data with at least one image mask to generate localized PET data, the PET data be co-registered to correspond to anatomical structures represented by the image mask, the processing arrangement further configured to generate a set of image intensity values (Ps) based on the localized PET data for voxels within a selected region of interest (ROI), each of the image intensity values corresponding to an intensity of the PET data for a corresponding one of the voxels, normalize the set of image intensity values (Ps) by generating a set of normalized values (Ns) where each corresponding N for each P is obtained using the formula: $N=(P-M)/S$, wherein M corresponds to a peak value for the set of image intensity values (Ps), and S corresponds to a spread for the set of image intensity values (Ps), and the processing arrangement further configured to generate a normalized PET image based on the set of normalized values (Ns).

* * * * *

UNITED STATES PATENT AND TRADEMARK OFFICE
CERTIFICATE OF CORRECTION

PATENT NO. : 10,945,685 B2
APPLICATION NO. : 16/521261
DATED : March 16, 2021
INVENTOR(S) : Yi Li, Jingyun Chen and Mony De Leon It is certified that error appears in the above-identified patent and that said Letters Patent is hereby corrected as shown below:

In the Specification

Column 1, Line 17:
Please delete "This invention was made with government support under NIH/NIA grants AG035137, AG032554, AG022374, and AG13616, AG12101, AG08051, NIH-HLB HL 111724. The U.S. Government has certain rights in the invention." and insert --This invention was made with government support under AG022374, AG008051, AG013616, HL111724, AG012101, AG032554, and AG035137 awarded by the National Institutes of Health. The government has certain rights in the invention.--.

Signed and Sealed this
Fifteenth Day of April, 2025

Coke Morgan Stewart
*Acting Director of the United States Patent and Trademark Office*